(12) United States Patent
Labyed et al.

(10) Patent No.: US 10,376,233 B2
(45) Date of Patent: Aug. 13, 2019

(54) DIFFRACTION SOURCE COMPENSATION IN MEDICAL DIAGNOSTIC ULTRASOUND VISCOELASTIC IMAGING

(71) Applicant: Siemens Medical Solutions USA, Inc., Malvern, PA (US)

(72) Inventors: Yassin Labyed, Maple Valley, WA (US); Liexiang Fan, Sammamish, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 429 days.

(21) Appl. No.: 15/094,883

(22) Filed: Apr. 8, 2016

(65) Prior Publication Data

US 2017/0290560 A1 Oct. 12, 2017

(51) Int. Cl.
*A61B 8/00* (2006.01)
*A61B 8/08* (2006.01)
*G01S 7/52* (2006.01)
*G01S 15/89* (2006.01)

(52) U.S. Cl.
CPC ............ *A61B 8/08* (2013.01); *A61B 8/485* (2013.01); *A61B 8/587* (2013.01); *G01S 7/5205* (2013.01); *G01S 7/52022* (2013.01); *G01S 7/52042* (2013.01); *G01S 7/52071* (2013.01); *G01S 15/8915* (2013.01)

(58) Field of Classification Search
CPC .......... A61B 8/08; A61B 8/485; A61B 8/587; G01S 15/8915; G01S 7/52071; G01S 7/5205; G01S 7/52022; G01S 7/52042
USPC ................................. 600/437–469
See application file for complete search history.

(56) References Cited

U.S. PATENT DOCUMENTS

| 6,508,768 B1 * | 1/2003 | Hall | A61B 8/08 600/443 |
| 6,558,324 B1 * | 5/2003 | Von Behren | A61B 8/08 600/437 |
| 8,469,891 B2 * | 6/2013 | Maleke | A61B 5/055 600/438 |
| 9,066,679 B2 * | 6/2015 | Beach | A61B 5/02007 |
| 9,603,583 B2 * | 3/2017 | Choi | G01S 15/8918 |

(Continued)

FOREIGN PATENT DOCUMENTS

| JP | 2015092937 A | 5/2015 |
| KR | 20140036650 A | 3/2014 |

(Continued)

OTHER PUBLICATIONS

Palmeri, Mark L., et al. "Acoustic radiation force based quantification of tissue shear modulus within the region of excitation." Ultrasonics Symposium, IEEE, 2008.

(Continued)

*Primary Examiner* — Sanjay Cattungal

(57) ABSTRACT

In viscoelastic imaging with ultrasound, the shear wave speed or other viscoelastic parameter is measured by tracking at the ARFI focal or other high-intensity location relative to the ARFI transmission. Rather than tracking the shear wave, the tissue response to ARFI is measured. A profile of displacements over time or a spectrum thereof is measured at the location. By finding a scale of the profile resulting in sufficient correlation with a calibration profile, the shear wave speed or other viscoelastic parameter may be estimated.

14 Claims, 6 Drawing Sheets

(56) References Cited

U.S. PATENT DOCUMENTS

| | | | |
|---|---|---|---|
| 9,726,647 B2* | 8/2017 | Walker | G01N 29/4418 |
| 2009/0056453 A1* | 3/2009 | McAleavey | A61B 8/08 |
| | | | 73/597 |
| 2009/0270730 A1* | 10/2009 | Azuma | A61B 8/0833 |
| | | | 600/443 |
| 2009/0292205 A1* | 11/2009 | Osaka | A61B 8/08 |
| | | | 600/443 |
| 2009/0304246 A1* | 12/2009 | Walker | G01S 7/52034 |
| | | | 382/128 |
| 2013/0102932 A1* | 4/2013 | Cain | A61N 7/00 |
| | | | 601/2 |
| 2013/0211253 A1* | 8/2013 | Hsu | G01S 15/8915 |
| | | | 600/438 |
| 2013/0218012 A1* | 8/2013 | Specht | A61B 8/485 |
| | | | 600/438 |
| 2014/0064021 A1* | 3/2014 | Nagae | G01S 7/52047 |
| | | | 367/7 |
| 2014/0064022 A1* | 3/2014 | Nagae | G01S 7/52047 |
| | | | 367/7 |
| 2014/0064023 A1* | 3/2014 | Nagae | G01S 7/52047 |
| | | | 367/7 |
| 2014/0276058 A1* | 9/2014 | Fan | A61B 5/4872 |
| | | | 600/442 |
| 2014/0330122 A1* | 11/2014 | Baghani | A61B 8/485 |
| | | | 600/438 |
| 2015/0133783 A1* | 5/2015 | Tabaru | A61B 8/485 |
| | | | 600/438 |
| 2015/0148673 A1* | 5/2015 | Yoshikawa | A61B 8/5223 |
| | | | 600/438 |
| 2015/0150535 A1 | 6/2015 | Fan et al. | |
| 2015/0182122 A1* | 7/2015 | Bamber | A61B 5/0095 |
| | | | 600/438 |
| 2015/0272547 A1* | 10/2015 | Freiburger | A61B 8/485 |
| | | | 600/438 |
| 2015/0305719 A1 | 10/2015 | Nenadic et al. | |
| 2015/0320394 A1* | 11/2015 | Arnal | G01S 7/52079 |
| | | | 600/427 |
| 2017/0112471 A1* | 4/2017 | Toji | A61B 8/485 |
| 2017/0360408 A1* | 12/2017 | Toji | A61B 8/469 |
| 2018/0296190 A1* | 10/2018 | Susumu | G01S 7/52022 |

FOREIGN PATENT DOCUMENTS

| | | |
|---|---|---|
| KR | 20150011275 A | 1/2015 |
| KR | 20150065158 A | 6/2015 |
| KR | 20150113925 A | 10/2015 |

OTHER PUBLICATIONS

Office action dated Mar. 21, 2018 in KR Application No. 10-2017-0044914, 15 pages, English translation attached.

\* cited by examiner

DIFFRACTION SOURCE COMPENSATION IN MEDICAL DIAGNOSTIC ULTRASOUND VISCOELASTIC IMAGING

BACKGROUND

The present embodiments relate to medical diagnostic ultrasound. In particular, ultrasound is used to estimate a viscoelastic parameter.

Conventional shear wave speed imaging uses an acoustic radiation force impulse (ARFI) or pushing pulse to generate shear waves. Ultrasound tracking at locations spaced laterally from the focus of the ARFI monitors the propagation of the shear wave away from the origin of the shear wave at the focus of the ARFI. Several factors affect the quality of the shear wave speed measurements, including loss of signal-to-noise ratio due to shear wave attenuation and spreading, reflections of the shear wave at boundaries and tissue heterogeneities, and motion artifacts due to transmission of multiple excitation pulses to track and/or increase the size of the imaging region. Furthermore, long cooling down times are necessary in order to stay within mechanical index (MI) and thermal United States Food and Drug Administration (FDA) limits.

BRIEF SUMMARY

By way of introduction, the preferred embodiments described below include a method, system, computer readable medium, and instructions for viscoelastic imaging with ultrasound. The shear wave speed or other viscoelastic parameter is measured by tracking at the ARFI focal or other high-intensity location relative to the ARFI transmission. Rather than tracking the shear wave, the tissue response to ARFI is measured. A profile of displacements over time or a spectrum thereof is measured at the location. By finding a scale of the profile resulting in sufficient correlation with a calibration profile, the shear wave speed or other viscoelastic parameter may be estimated.

In a first aspect, a method is provided for viscoelastic imaging with a medical diagnostic ultrasound scanner. The ultrasound scanner transmits from a transducer an acoustic radiation force impulse as a transmit beam with a beam profile along a scan line. A receive beamformer of the ultrasound scanner measures displacements as a function of time within the beam profile along the scan line. At least some of the displacements are responsive to the acoustic radiation force impulse. An image processor generates a first profile from the displacements for a first location, calculates a scale weighting of the first profile relative to a reference profile, and estimates a viscoelastic characteristic based on the scale weighting. A display generates an image of the viscoelastic characteristic.

In a second aspect, a system is provided for viscoelastic imaging. A transmit beamformer is configured to transmit an acoustic pushing pulse to a focal region in a patient. A receive beamformer is configured to output samples for the focal region of the patient. An image processor is configured to estimate shear wave speed at the focal region from the samples without tracking a shear wave in the patient. A display is configured to display the shear wave speed.

In a third aspect, a method is provided for viscoelastic imaging with a medical diagnostic ultrasound scanner. A beamformer of the ultrasound scanner tracks displacements along an axis of excitation of an acoustic radiation force impulse in a tissue of a patient. The displacements are caused by the acoustic radiation force impulse. An image processor of the ultrasound scanner estimates a viscoelastic parameter from the displacements along the axis and displacements from a phantom with a known viscoelastic value. The viscoelastic parameter is transmitted.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

To estimate shear wave speed and/or other viscoelastic parameters, ARFI-induced displacements at a location along the axis of excitation are measured. The optimal scaling factor to apply to the spectrum of the temporal displacement profile in order to match a spectrum of the displacement profile from a well-characterized phantom scanned using the same transmit-receive conditions as the tissue of interest is found. The optimal scaling factor may be found by matching the temporal displacement profiles rather than spectra.

In one embodiment, the shear wave speed or other viscoelastic parameter is estimated by using displacements tracked along the axis of excitation of ARFI push pulses (1) in the tissue of interest and (2) in a well-characterized tissue mimicking phantom scanned using the same transmit-receive conditions as the tissue of interest. Frequency-domain or time-domain analysis of the entire displacement profile, as opposed time-to-peak analysis of displacement profiles, is used. The shear wave speed is estimated by analyzing the displacement profile at one spatial location, as opposed to finding the time-to-peak of the displacement profile along depth. One calibrated tissue-mimicking phantom is used for the reference, but numerical simulations of a wide range of shear wave speeds may be used for the reference.

Due to measuring tissue response at the focal location or within the beam profile of the pushing pulse, higher spatial resolution and signal-to-noise ratio result. There may also be reduced acoustic output needed due to better signal-to-noise ratio and/or not having to deal with shear wave attenuation, resulting in shorter cooling down times. Since the shear wave is not tracked, there may be less susceptibility to motion artifacts due to shorter acquisition times.

Figure 1:
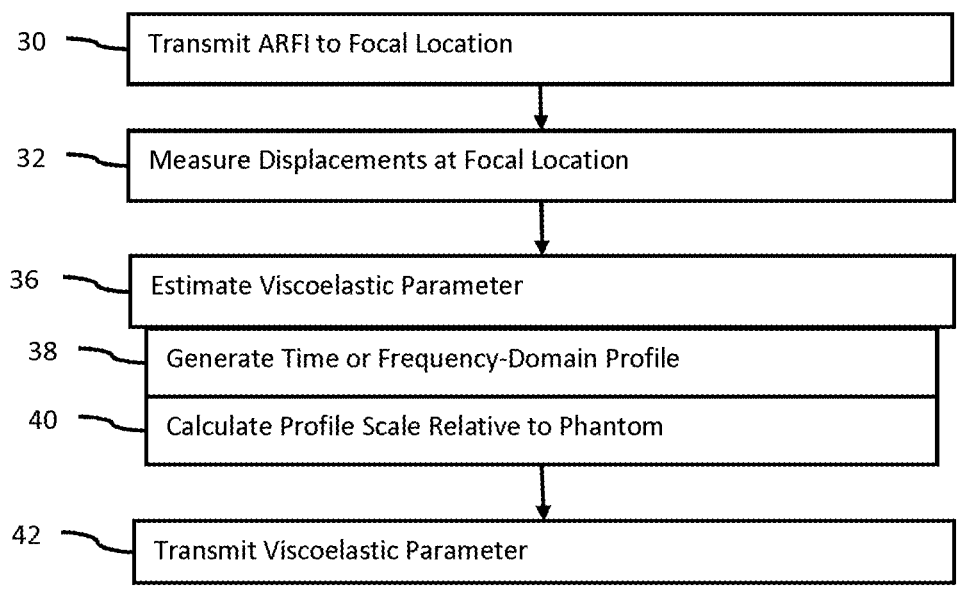
FIG. 1 is a flow chart of one embodiment of a method for viscoelastic imaging with a medical diagnostic ultrasound scanner.

FIG. 1 shows one embodiment of a flow chart diagram of a method for viscoelastic imaging with a medical diagnostic ultrasound scanner. Rather than tracking a shear wave, the displacement of tissue of a patient directly caused by the ARFI is tracked. The scale of these displacements or of a frequency transform of the displacements to match a calibrated profile is found. The scale and the viscoelastic value for the calibration are used to estimate the viscoelastic value for the tissue of the patient.

Figure 6:
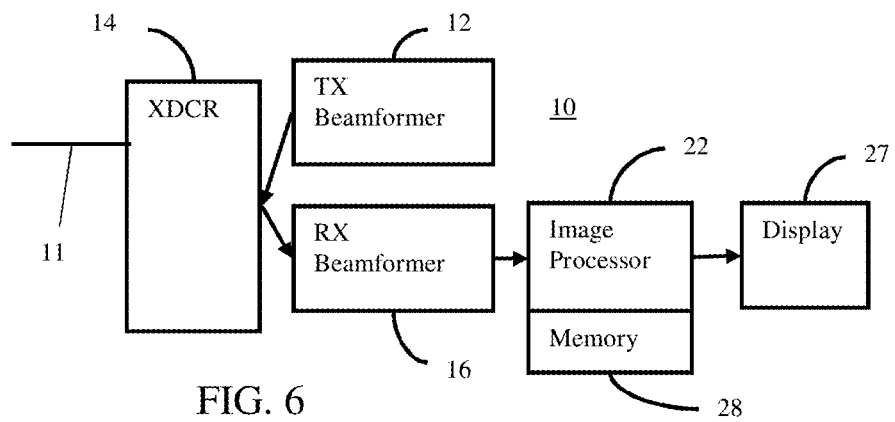
FIG. 6 is a block diagram of one embodiment of a system for viscoelastic imaging.

The method is performed by the ultrasound imaging system 10 of FIG. 6, the image processor 22, or a different system and/or processor. For example, the ultrasound imaging system 10 acquires samples for measuring displacement with the transmit and receive beamformers 12, 16 and the transducer 14, and the image processor 22 estimates the viscoelastic parameter from the samples. The display 27 displays the estimated viscoelastic parameter.

The acts of FIG. 1 are performed in the order shown (top to bottom) or a different order. For example, the samples for displacement are measured in act 32 prior to and after performing act 30.

Additional, different, or fewer acts than shown in FIG. 1 may be used. For example, act 42 is not performed. As another example, acts for scanning and generating B-mode or other ultrasound images are added.

In act 30, the ultrasound scanner uses the transducer to apply stress to the tissue. For example, ARFI focused at a region of interest or a point is transmitted. When the ARFI is applied to a focused area, a shear and/or longitudinal wave may be induced and propagate away from this focused area. These generated waves are not measured. The ARFI stresses the tissue. The tissue responds to the stress by moving, which is the movement that is measured. Relative to an original location or relaxed state, tissue is displaced. At the focal region or other locations within the transmit beam, this displacement increases and then recovers to zero, resulting in a temporal displacement profile. The tissue properties affect the displacement over time caused by the ARFI.

The impulse may be generated by a cyclical pulsed waveform of any number of cycles (e.g., tens or hundreds of cycles). For example, acoustic radiation force is transmitted as an impulse for applying stress to tissue. The impulse wavefront propagates to the region of interest, causing movement of the tissue.

Figure 2:
FIG. 2 is an example image showing a beam profile of an ARFI transmit beam.

FIG. 2 shows an example beam profile for an ARFI transmit beam. The ARFI transmit beam is transmitted along a scan line. The transmit beam has a profile relative to this scan line. The beam profile appears as a vertical column in this example of FIG. 2. A center of the column includes a region 46 of greater intensity. This region 46 includes the focal location of the transmit beam. The transmit beam has a beam profile marked by locations of greater acoustic intensity. The acoustic intensity decreases with further lateral and/or depth spacing from the focal region. The region 46 or beam profile may be defined based on an amount of reduction from a peak intensity, such as 3 dB, 6 dB, 10 dB, 20 dB or other amount of roll-off. Within the beam profile, greater acoustic intensity is provided.

Act 32 occurs while the tissue is being subjected to and/or recovers from the stress. For example, transmission and reception occurs after application or change in the stress and before the tissue reaches a relaxed state. For reference to determine magnitude of displacement, transmission and reception occurs prior to ARFI application and/or after the tissue relaxes to a steady state.

In act 32, the ultrasound scanner measures displacements over time. The ultrasound scanner uses a transmit beamformer to transmit a sequence of transmit beams. A plurality of ultrasound signals are transmitted to the tissue responding to the stress. The plurality of signals are transmitted in separate transmit events. A transmit event is a contiguous interval where transmissions occur without reception of echoes responsive to the transmission. During the phase of transmitting, there is no receiving. Where a sequence of transmit events is performed, a corresponding sequence of receive events is also performed in act 32. A receive beamformer of the ultrasound scanner generates samples in response to each transmit event. A receive event is performed in response to each transmit event and before the next transmit event.

For a transmit event, a transmit beam is formed. The pulses to form the transmit beams are of any number of cycles. For example, 1-3 cycles are used. Any envelope, type of pulse (e.g., unipolar, bipolar, or sinusoidal), or waveform may be used.

The transducer receives ultrasound echoes in response to each transmit event. The transducer converts the echoes to receive signals, which are receive beamformed into ultrasound data representing one or more spatial locations. The ultrasound scanner receives a sequence of receive signals where receive beams are received in response to each of the transmit beams in the transmit sequence.

The reception is interleaved with the transmission of the sequence. For each transmit event, a receive event occurs. The receive event is a continuous interval for receiving echoes from the depth or depths of interest. The event occurs after ceasing the transmit event. After the transducer completes generation of acoustic energy for a given transmission, the transducer is used for reception of the responsive echoes. The transducer is then used to repeat another transmit and receive event pair for the same spatial location or locations, providing the interleaving (e.g., transmit, receive, transmit, receive, . . . ) to measure the tissue response over time.

The measurement of displacements of the tissue is along an axis of excitation by the ARFI in the tissue of the patient. For example, the measurements are performed for the region 46, such as a focal location of the ARFI transmission. Rather than tracking outside the region 46 for laterally moving shear wave-caused displacements, the displacement directly caused by the ARFI at the focal location and/or other location in the region 46 of maximum acoustic intensity is measured. The samples for measuring displacements are acquired over time as the tissue displaces and within the beam profile along the scan line.

The response of tissue is detected at one or more depths along one or more scan lines. Doppler or B-mode scanning may be used for measuring motion of the tissue responding to the stress. Ultrasound imaging is performed before, during and/or after the ARFI stress is applied. Ultrasound data is received in response to transmissions of ultrasound. The transmissions and receptions are performed for a single spatial location (e.g., a focal point of the applied stress), along a line, over an area, or over a volume. A sequence of transmissions and receptions are provided for each spatial location to track over time. Using reception of multiple receive beams in response to each tracking transmission, data or samples for a plurality of laterally spaced locations and/or depths within the region 46 may be received simultaneously.

In one embodiment, the receive beams for measuring displacement are along the same scan line as the ARFI transmit beam. The transmit and receive beams for tracking are collinear with each other and the ARFI transmit beam. In other embodiments, the receive beams are at a different angle, but intersect the transmit scan line at the location where displacements are measured. In yet other embodiments, parallel receive beamformation is used. Two or more (e.g., 4) receive beams are formed in response to each transmit beam. The receive beams are within the region 46 but may be spaced from the transmit scan line, providing samples for a region about a location. Similarly, the depths for the samples used are within the region 46 at one or more depths. Whether for just one location or for multiple locations laterally and/or axially, the samples are positioned at locations having an acoustic intensity in the ARFI transmit beam that is at least 3 dB of location of a peak acoustic intensity in the ARFI transmit beam (e.g., focal depth location). For example, the locations are in the region 46. Locations outside the 3 dB intensity may be used.

The beamformed data or samples are acquired as the tissue undergoes displacement. Some samples of the tissue in the relaxed state may be acquired. For example, the samples are acquired prior to application of the ARFI and after application of the ARFI. Prior to application, the tissue may be in a relaxed state or free of displacement. Once the ARFI transmission occurs, the tissue is moved so that subsequent samples are of the tissue in the displaced state until the tissue returns to a relaxed state. The sampling occurs over any range of times, such as starting before or after the ARFI transmit beam and continuing for any amount of time after ARFI ceases. The samples are acquired at a plurality of times.

The samples are radio frequency (RF) or in-phase and quadrature (IQ) data output by a receive beamformer. In response to a transmission of acoustic energy (e.g., a transmit beam), acoustic echoes impinge upon elements of a transducer. The elements convert the acoustic echoes into electrical signals. The receive beamformer coherently sums the signals from different elements to determine the response of tissue at particular sample locations. The output of the receive beamformer is RF or IQ data.

The displacements are measured from the samples. The ultrasound scanner determines tissue motion. Tissue motion is detected as a displacement in one, two, or three dimensions. Motion responsive to the ARFI transmit beam may be detected. The tissue motion is detected at different times. The different times correspond to the different tracking scans (i.e., transmit and receive event pairs).

A reference sample or samples are acquired with the tissue in the relaxed data and are used to determine displacement at other times. Tissue motion is detected by estimating displacement relative to the reference tissue information. For example, the displacement of tissue along one or more receive scan lines is determined. The displacement may be measured from tissue data, such as B-mode ultrasound data, but flow (e.g., velocity) or IQ information prior to detection may be used.

Correlation, cross-correlation, minimum sum of absolute differences or other similarity measure is used to determine the displacement between scans (e.g., between the reference and the current). Data representing spatial locations distributed about a location of measurement is correlated with the reference data. For each depth or spatial location, a correlation over a plurality of depths or spatial locations is performed. The spatial offset with the highest or sufficient correlation at a given time indicates the amount of displacement. For each location, the displacement as a function of time is determined.

Two or three-dimensional displacement in space may be used. One-dimensional displacement along a direction different from the scan lines or beams may be used.

The measurements are performed for any number of scan lines. For example, four receive beams are formed in response to each transmission. For each depth, the displacements from different receive beams may be combined, such as averaged. In other embodiments, only a single receive beam or other numbers of receive beams are formed in response to each transmission.

After transmitting the acoustic force to generate the shear wave, B-mode transmissions and receptions are performed repetitively along any number of scan lines within the region 46. Some of the ultrasound data, such as at the beginning or end of the repetitions, may not be responsive to the tissue displacement, so is similar to the reference. Each repetition monitors a same region or locations for determining tissue response for those locations. By repeating the transmitting of the ultrasound pulses and the receiving of the ultrasound echoes over the time, the displacements over the time are determined. The measurement is repeated. The repetition is for different transmit and receive events. Any number of M repetitions may be used, such as repeating about 50-100 times. The repetitions occur as frequently as possible while the tissue recovers from the stress, but without interfering with reception. The tissue temporal displacement profile is obtained by repeatedly transmitting to and receiving signals from the same target area in a similar way as the Doppler method does.

Figure 3:
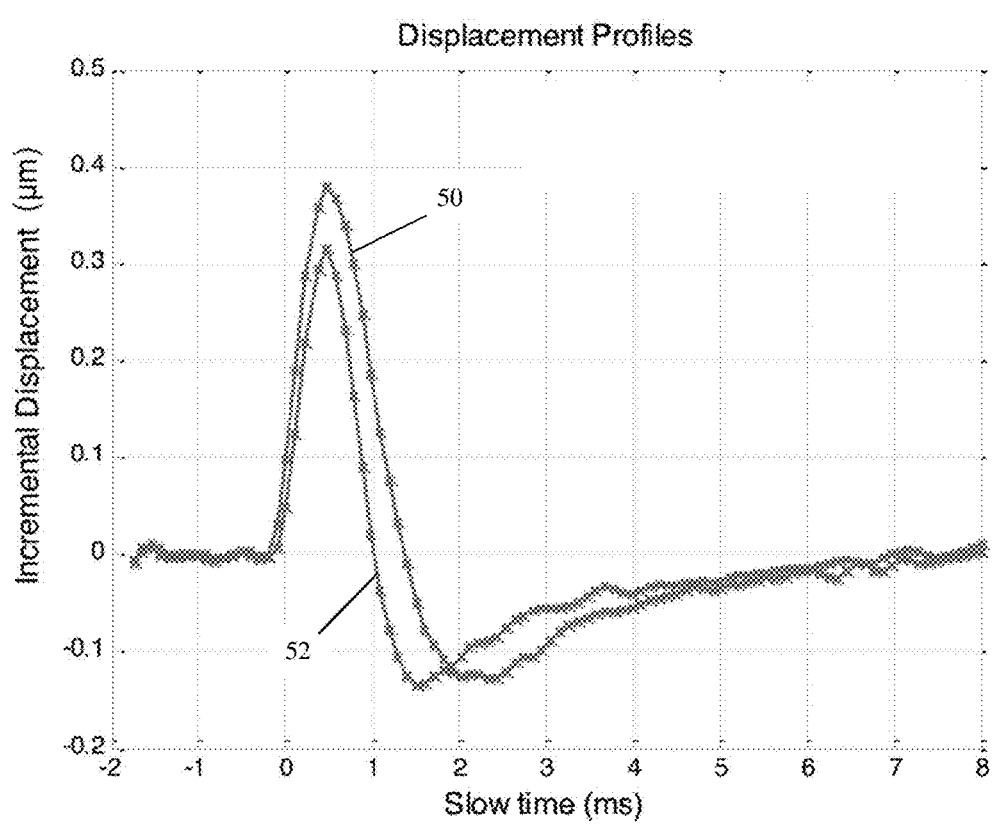
FIG. 3 shows example time-domain displacement profiles of a phantom mimicking tissue in a patient and of a reference phantom.

FIG. 3 shows an example displacement profile 52. Instead of using absolute displacement, FIG. 3 shows incremental displacement between pairs of successive times. The tissue continues to displace while the incremental displacement is positive, and starts to relax when the incremental displacement becomes negative. The true or absolute displacement, which is the integral of the incremental displacement, may be used in other embodiments.

The displacement is measured from a phantom for FIG. 3, but would be measured from sampled tissue of a patient. Time 0 is the time of the ARFI transmit beam. Times—2.0 to 0.0 milliseconds are displacements measured at a focal region of the ARFI transmit beam prior to transmission. Times 0.1-8.0 milliseconds are displacements measured at the focal region of the ARFI transmit beam after transmission. The tissue in the region 46 generally displaces due to the ARFI rather than a shear or longitudinal wave generated by the ARFI transmit beam. This displacement is around 0 prior to the ARFI transmit beam, then increases to about 0.3 µm within a fraction of a millisecond, then moves back towards and passes the relaxed state during times 0.4-1.5 milliseconds. After 1.5 milliseconds, the displacement progresses towards the relaxed state.

FIG. 3 also shows a displacement profile 50 for a phantom. Using the same ARFI transmit beam and measurement (e.g., same transmit and receive tracking events), the displacement profile for a phantom with a known elasticity is measured. For example, the displacement profile 50 of FIG. 3 is of a 5 kPa phantom with a 1.25 m/s shear velocity. Other calibration sources may be used, such as live or dead tissue with a known shear velocity.

The displacement profile or a spectrum of the displacement profile used for calibration may be measured by the ultrasound scanner or may be measured by a different ultrasound scanner. This calibration profile is stored in the ultrasound scanner.

Referring again to FIG. 1, an image processor of the ultrasound scanner estimates a viscoelastic parameter from the displacements in act 36. Displacements measured over time for one or more locations along the axis represented by the ARFI region 46 are used. The displacements from the phantom with the known viscoelastic value are also used. The displacement profiles 50 and 52 of FIG. 3 are one example of the displacements used for estimating the viscoelastic parameter. The displacements are for a focal location of the ARFI transmit beam, but may be for other locations within the region 46. Where displacements are provided for multiple locations within the region 46, the displacements for the same times may be averaged.

Acts 38 and 40 are one example for estimating the viscoelastic parameter in act 36. Additional, different, or fewer acts may be provided to estimate from the displacements.

In act 38, the image processor generates a profile. The profile is generated from the displacements for a given location or region. The profile is a graph, collection of measures, and/or curve fit to the measures. The profile is a measure of amplitude along one axis and time or frequency along another axis.

In one embodiment, the profile is a time-domain profile. The displacements as a function of time are used. For example, the curve 52 and/or the displacements as a function of time of FIG. 3 are used. The displacement amplitude as a function of time is generated.

Figure 4:
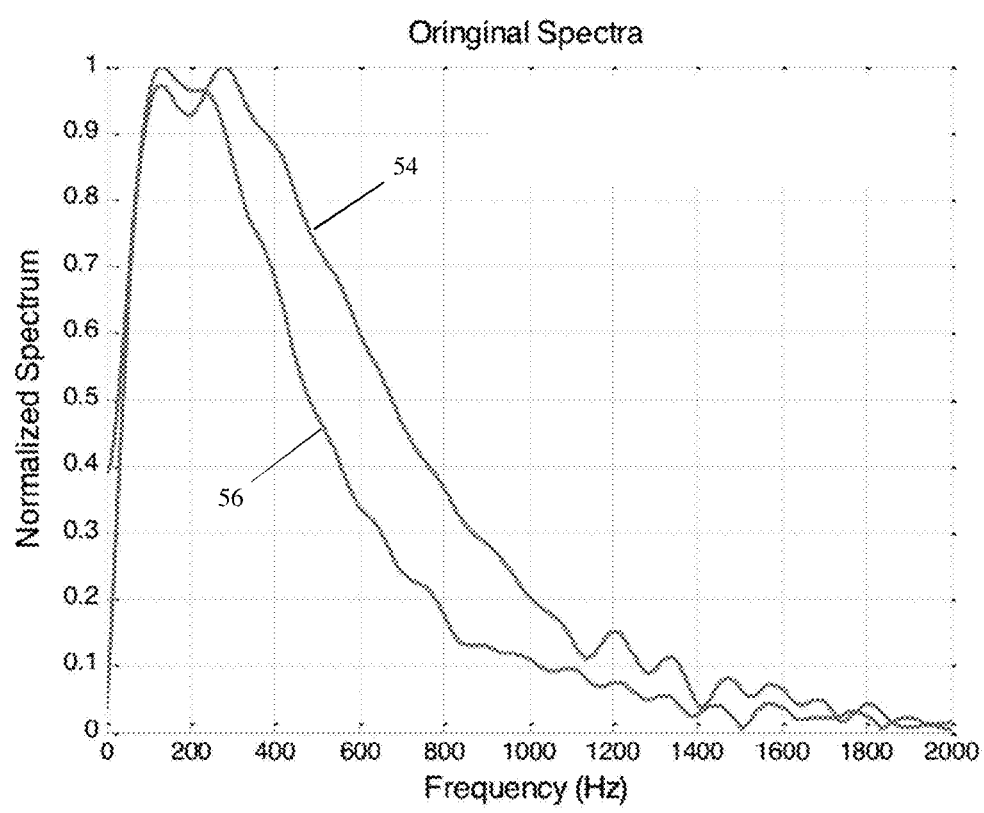
FIG. 4 shows example spectra for the profiles of FIG. 3.

In another embodiment, the profile is a spectrum. An amplitude spectrum of the displacements as a function of time is generated. The displacements as a function of time are transformed into the frequency domain. The ultrasound scanner or a transform processor applies a Fourier (e.g., Fast Fourier Transform) or other transform to the displacements. The transform results in a spectrum for the location. Where displacement profiles are provided for multiple locations, the displacements for each time are averaged or the spectra from transforms for each location are averaged.

Where the transform is applied to generate the profile, a transform is also used for the calibration source. FIG. 4 shows an example. The displacement profiles 50, 52 from FIG. 3 are transformed. The resulting spectrum 56 for the tissue displacements (phantom mimicking tissue in this case) is shown with the resulting spectrum 54 from the calibration source (another phantom in this case). In FIG. 4, the spectra 54, 56 are normalized. For example, the amplitudes are divided by the maximum amplitude. In other embodiments, normalization is not used. Since the phantom is stiffer than the tissue (e.g., 5 kPa verses 10 kPa in this example), the spectrum 54 for the calibration phantom has a broader bandwidth. The spectrum for calibration may have a narrow bandwidth.

In act 40 of FIG. 1, the image processor calculates a scale weighting of the profile 52, 56 from tissue relative to the reference profile 50, 54. The scale weighting is a scale factor adjusting an axis, such as the temporal or frequency axis. The profile 52, 56 is stretched or shrunk uniformly in time or frequency. The x-axis is rescaled, and the scale weighting indicates the magnitude of the change or scaling.

In FIGS. 3 and 4, the magnitude and time or frequency content of the profiles 50-56 are different. Since the same ARFI and measurement transmit and receive operations are used, the difference is due to differences in the scanned material. The differences in the scanned material may be quantified or represented by shear velocity and/or elasticity. By determining an amount of difference, the shear velocity and/or elasticity may be estimated.

The shear wave speed and/or elasticity is estimated in act 36 by finding in act 40 the optimal scaling factor of the profile 52, 56 from tissue to the profile 50, 54 from the phantom or other calibration tissue. The optimal time scaling factor for the on-axis displacement profile 52 from tissue or frequency scale factor of the spectrum 56 from tissue to match to the calibration profile is found.

To find the optimal scaling factor, a correlation of the profile 52, 56 from tissue as scaled to the profile 50, 54 from the calibration source is calculated. The x-axis (time or frequency) is scaled to maximize the correlation. The x-axis is scaled by different amounts and the results of the scaling are correlated, providing a correlation measure for each amount of scaling. The scaling and correlation are repeated in order to find the optimal scale factor.

Other similarity measures than correlation may be used. Any search pattern to identify the maximum may be used. In alternative embodiments, a sufficient (e.g., above a threshold) correlation is found rather than the maximum.

Figure 5:
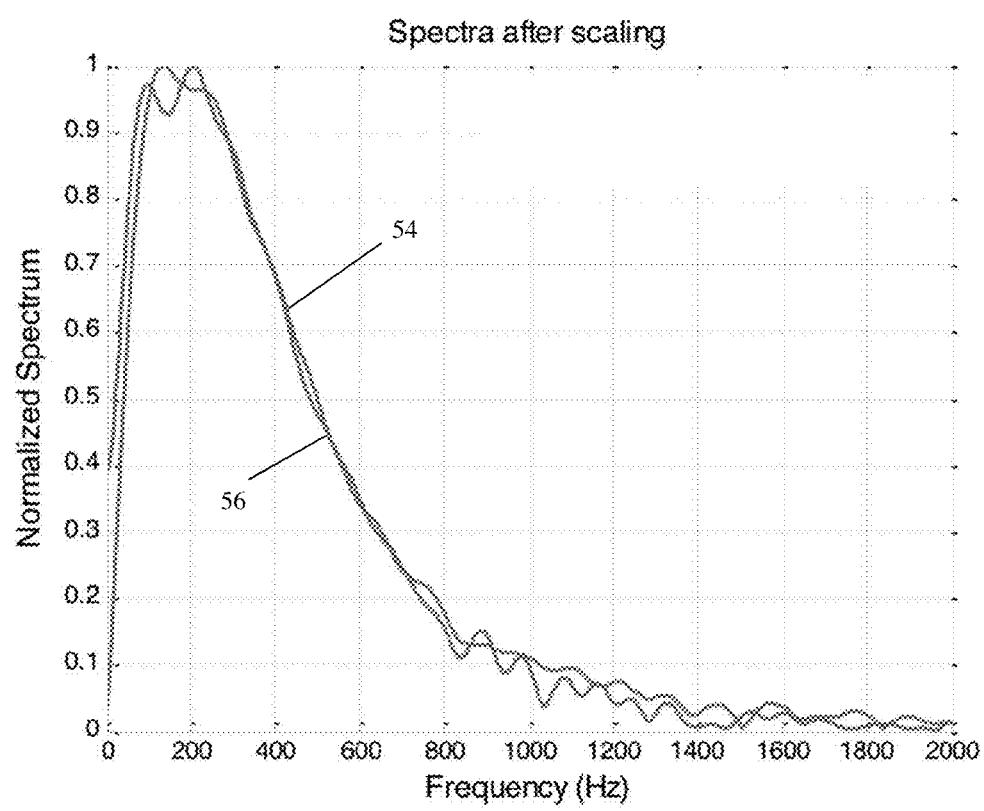
FIG. 5 shows the example spectra of FIG. 4 with the spectrum for the measured profile of mimicked tissue scaled to more strongly correlate with the spectrum of the reference phantom.

FIG. 5 shows an example of finding the scale factor, c, using the spectra 54, 56 of FIG. 4. The normalized spectrum 54 of the reference and the scaled normalized spectrum of the mimicked tissue sample 56 are matched. For example, the spectrum 56 of FIG. 4 is scaled by 1.36 to match, resulting in the overlap and corresponding greater and/or greatest correlation shown in FIG. 5.

The scaling resulting in the greatest or sufficient match or correlation is selected. After determining the amount of similarity of the spectrum 56 subjected to different scaling, the scaling with the greatest correlation is identified. This scale factor is saved or used to estimate the viscoelastic characteristics of the sampled tissue.

Using the spectra as the profiles, $A_{sample}(f)$ is the displacement spectrum of the tissue sampled on-axis (e.g., in the region 46). $A_{ref}(f)$ is the displacement spectrum of the reference or calibration source. Since the transmit-receive conditions for the tissue and the reference or calibration are the same, then $A_{ref}(f)=A_{sample}(f)$. The scale factor or weighting, c, is equal to the ratio of the shear wave velocity of the reference or calibration source, $v_{ref}$, to the shear wave velocity of the sampled tissue, $v_{sample}$: $c=v_{ref}/v_{sample}$.

The image processor estimates the viscoelastic characteristic based on the scale weighting, c. Given that the shear wave velocity of the reference or calibration source is known and the scale factor, c, is measured for the tissue sample, the shear wave velocity for the tissue sample is calculated. In the example of FIG. 5, the scale factor is 1.36 and the known or calibrated shear wave speed is 1.25 m/s. As a result, the shear wave speed for the sampled tissue is 1.7 m/s.

In the example of FIGS. 3-5, the sampled tissue is mimicked as a 10 kPa phantom and the reference or calibration source is a 5 kPa phantom. In another example where the sampled tissue is mimicked as a 20 kPa phantom, c is measured as 2.08, resulting in $v_{sample}=2.6$ m/s. In yet another example where the sampled tissue is mimicked as a 40 kPa phantom, c is measured as 2.72, resulting in $v_{sample}=3.4$ m/s. As expected, the velocity in the higher kPa phantoms is higher.

Other viscoelastic parameters or characteristics may be estimated. For example, the known relationship of shear wave speed to elasticity is used to determine the elasticity. $G=E/3=Vs^2$ where G is the Shear modulus, E is Young's modulus, and Vs is the shear wave speed.

Using the profiles as the displacements in the time-domain, the same calculations are used. The scale factor is determined by correlation and used to calculate the shear wave velocity for the sampled tissue.

By measuring tissue displacement, such as during relaxation of the tissue after being forced to move by ARFI, the viscoelastic parameter is estimated. The measurement is of the displacement directly caused by the ARFI rather than of a shear or longitudinal wave generated by the ARFI. As a result, the measurement is performed at the focal point of the ARFI transmission or other locations in higher acoustic intensity region 46 of the ARFI transmit beam. This results in a higher signal-to-noise ratio and/or less acoustic energy being used as compared to measuring the shear velocity from tracking a shear wave at laterally spaced locations.

In another embodiment, the frequency-dependent scale weighting is calculated. Rather than a single scale factor for uniform scaling, a frequency-dependent scale factor is found. A time-dependent scaling factor may be used. Viscosity of tissue may cause the speed at different frequencies to be different. The shift in a given frequency to match the normalized amplitudes of the spectral profiles 54, 56 is found for any frequency or frequencies. The variation in scaling as a function of frequency or the shift itself for a given frequency is used as the scale factor. The scaling factor may vary linearly with frequency, implying that the shear wave speed varies linearly with frequency and allowing estimation of the slope and/or intercept as a function of frequency. A separate scale factor may be determined for each frequency. Shear wave speed as a function of frequency may be determined. The variation in speed over frequency may be used to calculate other viscoelastic parameters.

In act 42, the image processor, a display, a communications interface, or other device transmits the viscoelastic parameter. The transmission is from and/or within the ultrasound scanner. The transmission is to another device, such as a memory, display, network, server, workstation, patient record database, and/or picture archiving and communications server. The viscoelastic parameter is transmitted as data or imbedded in an image.

In one embodiment, the transmission is to a display. A value that is a function of the viscoelastic parameter is displayed. The value is displayed as alphanumeric text. The value is the viscoelastic parameter itself (e.g., shear wave speed) and/or is derived from the viscoelastic parameter. In alternative or additional embodiments, the value is included as part of a graph, such as displaying the viscoelastic parameter as a function of frequency or location.

In another embodiment, the value is part of an image spatially representing the viscoelastic parameter. For example, the shear wave speed is measured at two or more different locations. Acts 32-40 are repeated for more than one location in the region 46. In response to one ARFI transmission, the tissue displacements at different locations in the transmit beam profile of the ARFI transmission are measured and used to estimate location specific shear wave speed. Alternatively or additionally, acts 30-40 are repeated for different regions 46. The ARFI transmit is repeated for different tissue locations. For each ARFI transmit beam, displacements are measured for one or more locations. The values of the shear wave speed for the different locations modulate the color, brightness, and/or shade of the image. Different pixels in the image show the corresponding viscoelastic values through this modulation.

The value is displayed alone or with another image. For example, a B-mode image or other image is provided with the value or values representing the relationship. Where the viscoelastic characteristic is measured for multiple locations, a color or other modulation in a region of interest in the B-mode image is displayed. Where the viscoelastic characteristic is measured for one or more locations, alphanumeric text showing the value or values is provided as an annotation or overlay on the B-mode image.

FIG. 6 shows one embodiment of a medical system 10 for viscoelastic imaging. The medical system 10 implements the method of FIG. 1 or another method. The medical system 10 is an ultrasound scanner using measures of tissue displacement due to ARFI rather than shear or longitudinal wave induced by the ARFI. By scaling measured displacements in the time or frequency domain and correlating with a calibrated measure, a value for a viscoelastic characteristic is estimated for diagnostic use by a physician.

The medical system 10 includes a transmit beamformer 12, a transducer 14, a receive beamformer 16, an image processor 22, a memory 28, and a display 27. Additional, different or fewer components may be provided. For example, the medical system 10 includes a B-mode or other detector. As another example, the image processor 22, memory 28, and/or display 27 are provided without the front-end components, such as the transmit and receive beamformers 12, 16. In yet another example, a user interface including a user input (e.g., mouse, trackball, keyboard, buttons, knobs, sliders, and/or touch pad) is provided for user indication of a region of interest on an image.

In one embodiment, the medical system 10 is a medical diagnostic ultrasound system. In an alternative embodiment, the system 10 is a computer or workstation.

The transducer 14 is an array of a plurality of elements. The elements are piezoelectric or capacitive membrane elements. The array is configured as a one-dimensional array, a two-dimensional array, a 1.5D array, a 1.25D array, a 1.75D array, an annular array, a multidimensional array, a wobbler array, combinations thereof, or any other now known or later developed array. The transducer elements transduce between acoustic and electric energies. The transducer 14 connects with the transmit beamformer 12 and the receive beamformer 16 through a transmit/receive switch, but separate connections may be used in other embodiments.

The transmit and receive beamformers 12, 16 are a beamformer for scanning with the transducer 14. The transmit beamformer 12, using the transducer 14, transmits one or more beams into a patient. Vector®, sector, linear or other scan formats may be used.

The transmit beamformer 12 is a processor, delay, filter, waveform generator, memory, phase rotator, digital-to-analog converter, amplifier, combinations thereof or any other now known or later developed transmit beamformer components. In one embodiment, the transmit beamformer 12 digitally generates envelope samples. Using filtering, delays, phase rotation, digital-to-analog conversion and amplification, the desired transmit waveform is generated. Other waveform generators may be used, such as switching pulsers or waveform memories.

The transmit beamformer 12 is configured as a plurality of channels for generating electrical signals of a transmit waveform for each element of a transmit aperture on the transducer 14. The waveforms are unipolar, bipolar, stepped, sinusoidal, or other waveforms of a desired center frequency or frequency band with one, multiple, or fractional number of cycles. The waveforms have relative delay and/or phasing and amplitude for focusing the acoustic energy. The transmit beamformer 12 includes a controller for altering an aperture (e.g. the number of active elements), an apodization profile (e.g., type or center of mass) across the plurality of channels, a delay profile across the plurality of channels, a phase profile across the plurality of channels, center frequency, frequency band, waveform shape, number of cycles, and/or combinations thereof. A transmit beam origin, orientation, and focus are generated based on these beamforming parameters.

The transmit beamformer 12 generates a transmit beam for ARFI and for measuring resulting displacements. The transmit beams are formed at different energy or amplitude levels. Amplifiers for each channel and/or aperture size control the amplitude of the transmitted beam. Transmit beams to displace tissue may have greater amplitudes than for imaging or measuring tissue displacement. Alternatively or additionally, the number of cycles in the pulse or waveform used to generate ARFI is greater than for tracking (e.g., 100 or more cycles for ARFI and 1-6 cycles for tracking).

The ARFI transmit beam is transmitted as an acoustic pushing pulse. The transmit beam is focused at a location, causing increased acoustic intensity at the location and surrounding locations along a scan line. Similarly, transmit beams for measuring the tissue displacement at the focal location or locations of increased intensity of the ARFI transmission are generated along the same scan line and/or to the same locations.

The receive beamformer 16 is a preamplifier, filter, phase rotator, delay, summer, base band filter, processor, buffers, memory, combinations thereof or other now known or later developed receive beamformer components. The receive beamformer 16 is configured into a plurality of channels for receiving electrical signals representing echoes or acoustic energy impinging on the transducer 14. A channel from each of the elements of the receive aperture within the transducer 14 connects to an amplifier and/or delay. An analog-to-digital converter digitizes the amplified echo signal. The digital radio frequency received data is demodulated to a base band frequency. Any receive delays, such as dynamic receive delays and/or phase rotations, are then applied by the amplifier and/or delay. A digital or analog summer combines data from different channels of the receive aperture to form one or a plurality of receive beams. The summer is a single summer or cascaded summer. In one embodiment, the beamform summer is configured to sum in-phase and quadrature channel data in a complex manner such that phase information is maintained for the formed beam. In alternative embodiments, the receive beamformer sums radio frequency data. Other receive beamformers may be used.

The receive beamformer 16 is configured to form receive beams in response to the transmit beams. For example, the receive beamformer 16 receives one, two, or more receive beams in response to each transmit beam for measuring. The phase rotators, delays, and/or summers may be repeated for parallel receive beamformation. One or more of the parallel receive beamformers may share parts of channels, such as sharing initial amplification. The receive beams are collinear, parallel and offset or nonparallel with the corresponding transmit beams.

The receive beamformer 16 is configured to output samples for a single location or multiple locations in a patient. The receive beamformer 16 outputs samples representing the one or more locations within the higher intensity region 46 of the ARFI transmit beam. The samples are on-axis, such as at one or more depths by the ARFI scan line or locations in the high intensity region 46 alongside the ARFI scan line. While the locations are relative to the ARFI transmit beam, samples from echoes of the ARFI transmit beam are not formed. The samples are from echoes of transmit beams transmitted for measuring tissue displacement.

Once the channel data is beamformed or otherwise combined to represent one or more locations along the scan line 11, the data is converted from the channel domain to the image data domain. By repeating the transmit and receive operations, samples representing the location over time are acquired. Beamformed samples for measuring tissue displacement caused by the ARFI at the focal region are output.

The image processor 22 is a digital signal processor, a general processor, an application specific integrated circuit (ASIC), field programmable gate array (FPGA), control processor, digital circuitry, analog circuitry, graphics processing unit, combinations thereof, or other now known or later developed device for measuring displacements from beamformed samples and estimating shear wave speed or other viscoelastic parameter from the displacements. The image processor 22 is configured by hardware, firmware, and/or software, such as operating pursuant to instruction provided in the memory 28 or a different memory. In one embodiment, the image processor 22 is a digital signal processor, ASIC, or FPGA specifically for applying a Fourier transform, and another device (e.g., calculator or processor) for calculating the viscoelastic parameter. In other embodiments, the image processor 22 is a programmable device that performs both the transform and calculation.

In one embodiment, the image processor 22 is configured to estimate shear wave speed at the focal region of the ARFI transmit beam from the samples representing the focal region. This estimation is based on displacement of the tissue caused by ARFI, not the induced shear wave. Without tracking a shear wave in the patient, the image processor 22 estimates the shear wave speed from displacements in the ARFI focal or high intensity region.

The image processor 22 generates displacements from the beamformed samples. Using correlation or other similarity measure, the amount of tissue displacement at the location from a reference scan of the tissue is determined. The displacement is determined for each of a plurality of times, providing a displacement profile. The image processor 22 may apply a Fourier transform to convert the displacement profile (displacement as a function of time) into a spectrum.

Using the displacement or the spectrum profile, the image processor 22 calculates a scale factor for the time or frequency of the displacements. Different scale factors are applied to the profile from the samples. The resulting curves are fit to a curve or measures from a calibration source, such as a phantom. The scale factor resulting in a sufficient or greatest correlation is selected. In other embodiments, the image processor 22 calculates a frequency-dependent scale factor.

The image processor 22 is configured to estimate the shear wave speed from the scale factor and a known speed for the phantom or other calibration source. The ratio of velocities of the sampled tissue and the calibration is equal to the scale factor, so the measured scale factor and the known speed for the calibration are used to calculate the shear wave speed of the sampled tissue. In other embodiments, the shear wave speed from a frequency-dependent scale factor is estimated. The shear wave speeds at different frequencies may be estimated.

The samples or other ultrasound data may be used to generate an image. A B-mode detector, flow estimator (e.g., Doppler processor), or other detector may be provided for detecting characteristics from the receive beamformed samples. A B-mode detector detects the intensity or power of the acoustic backscatter. A flow estimator detects the velocity, energy, or variance of moving objects (e.g., tissue or fluid). The detection may be used to generate an image from which a region of interest for viscoelastic parameter measurement is selected.

The detector, estimator, and/or the image processor 22 are configured to generate an image. The image includes the viscoelastic parameter. For example, a graph of the shear wave speed by location or as a function of frequency is generated as an image. As another example, alphanumeric text is generated as an image, such as "shear wave velocity=3.4 m/s." In other embodiments, the viscoelastic value is provided as an annotation on an image of the patient, such as on a B-mode image. In yet other embodiments, one or more pixels corresponding to locations at which the viscoelastic parameter is estimated are modulated, such as with color, to show the value or values of the viscoelastic parameter.

The memory 28 is video random access memory, random access memory, removable media (e.g. diskette or compact disc), hard drive, database, or other memory device for storing data. The memory 28 is used by the image processor 22 for storing samples, displacements, a spectrum, correlation results, a scale factor, a calibration profile (e.g., displacements as a function of time or a spectrum thereof), a known viscoelastic parameter, and/or an estimated viscoelastic parameter.

The instructions for implementing the processes, methods and/or techniques discussed above are provided on computer-readable storage media or memories, such as a cache, buffer, RAM, removable media, hard drive or other computer readable storage media, such as represented by the memory 28. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The display 27 is a CRT, LCD, plasma, projector, monitor, printer, touch screen, or other now known or later developed display device. The display 27 receives RGB, other color values, or other values and outputs an image. The image may be a gray scale or color image. The image displays information that is a function of the viscoelastic parameter, such as showing shear wave speed. Alphanumeric, graphical, annotation, or other representation of the viscoelastic parameter or values derived from the viscoelastic parameter is displayed in an image on the display 27. The image may or may not additionally represent the region of the patient scanned by the beamformer 12, 16 and transducer 14.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for viscoelastic imaging with a medical diagnostic ultrasound scanner, the method comprising:
   transmitting from a transducer an acoustic radiation force impulse by the ultrasound scanner as a transmit beam with a beam profile along a scan line;
   measuring, by a receive beamformer of the ultrasound scanner, displacements as a function of time within the beam profile along the scan line, at least some of the displacements responsive to the acoustic radiation force impulse;
   generating, by an image processor, a first profile from the displacements for a first location;
   calculating, by the image processor, a scale weighting of the first profile relative to a reference profile;
   estimating, by the image processor, a viscoelastic characteristic based on the scale weighting; and
   generating on a display an image of the viscoelastic characteristic.

2. The method of claim 1 wherein measuring comprises measuring with receive beams collinear with the scan line.

3. The method of claim 1 wherein measuring comprises measuring with simultaneous receive beams along receive lines that are positioned at locations with intensities within 3 dB below a peak intensity of the transmit beam within the beam profile.

4. The method of claim 1 wherein measuring comprises scanning before the transmitting of the acoustic radiation force impulse and measuring a plurality of times after the transmitting of the acoustic radiation force impulse.

5. The method of claim 1 wherein measuring comprises measuring the displacements as tissue relaxes after ceasing of the acoustic radiation force impulse at a focal location of the acoustic radiation force impulse.

6. The method of claim 1 wherein generating the first profile comprises generating the first profile as a time-domain profile of the displacements as a function of the time.

7. The method of claim 1 wherein generating the first profile comprises generating a spectrum of the displacements as a function of the time.

8. The method of claim 1 wherein calculating the scale weighting comprises scaling an axis of the first profile to maximize a correlation with the reference profile.

9. The method of claim 1 wherein calculating the scale weighting comprises scaling a time or frequency of the first profile by different amounts, correlating results of each scaling amount with the reference profile, and selecting the scaling with a greatest correlating.

10. The method of claim 1 wherein calculating the scale weighting comprises calculating a frequency-dependent scale weighting.

11. The method of claim 1 wherein estimating the viscoelastic characteristic comprises estimating elasticity.

12. The method of claim 1 wherein estimating the viscoelastic characteristic comprises estimating shear wave velocity with the measuring being of tissue relaxation from the acoustic radiation force impulse and not a shear wave.

13. The method of claim 1 wherein estimating comprises estimating as a function of the scale weighting and a known characteristic of a calibration phantom associated with the reference profile.

14. The method of claim 1 wherein generating comprises generating the image with a pixel modulation, graph, or alphanumeric text for the viscoelastic characteristic.

\* \* \* \* \*